United States Patent
Feng et al.

(10) Patent No.: US 8,986,400 B2
(45) Date of Patent: Mar. 24, 2015

(54) FUELS AND FUEL ADDITIVES PRODUCTION FROM GLYCEROL CONVERSION USING A MONOHYDRIC ALCOHOL AND HETEROGENEOUS CATALYSIS

(71) Applicant: Southwest Research Institute, San Antonio, TX (US)

(72) Inventors: Maoqi Feng, San Antonio, TX (US); Chee-Kai Tan, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 198 days.

(21) Appl. No.: 13/653,941

(22) Filed: Oct. 17, 2012

(65) Prior Publication Data

US 2014/0101988 A1    Apr. 17, 2014

(51) Int. Cl.

| | |
|---|---|
| *C10L 1/185* | (2006.01) |
| *C10L 1/182* | (2006.01) |
| *C07C 41/01* | (2006.01) |
| *C07C 29/60* | (2006.01) |
| *C10L 1/19* | (2006.01) |
| *C07D 307/20* | (2006.01) |
| *C07C 67/00* | (2006.01) |
| *C07C 41/09* | (2006.01) |

(52) U.S. Cl.
CPC .................. *C10L 1/191* (2013.01); *C07C 41/01* (2013.01); *C07C 29/60* (2013.01); *C07D 307/20* (2013.01); *C07C 67/00* (2013.01); *C10L 1/1852* (2013.01); *C10L 1/1824* (2013.01); *C10L 1/1826* (2013.01); *C07C 41/09* (2013.01)

USPC .................. 44/443; 44/447; 44/448; 44/451; 568/622; 568/623; 568/671; 568/672; 568/679

(58) Field of Classification Search
USPC ............ 44/447, 448, 451; 568/622, 623, 671, 568/679, 672
See application file for complete search history.

(56) References Cited

U.S. PATENT DOCUMENTS

| | | | |
|---|---|---|---|
| 4,115,424 A | 9/1978 | Unland et al. | |
| 4,859,696 A | 8/1989 | Kamiya et al. | |
| 5,308,365 A | 5/1994 | Kesling, Jr. et al. | |
| 7,671,124 B2 | 3/2010 | Tsujimoto et al. | |
| 8,058,484 B2 * | 11/2011 | Abhari | 568/861 |
| 8,070,836 B2 * | 12/2011 | Ng et al. | 44/308 |
| 8,075,642 B2 * | 12/2011 | Dumesic et al. | 44/308 |

(Continued)

OTHER PUBLICATIONS

Htun, et al Preparation of Zeolite (NaX,Faujasite) From Pure Silica And Alumina Sources; International Conference on Chemical Processess and Environmental issues (ICCEEI'2012) Jul. 15-16, 2012, Singapore, 212-216.

(Continued)

*Primary Examiner* — Ellen McAvoy
(74) *Attorney, Agent, or Firm* — Grossman, Tucker et al.

(57) ABSTRACT

The present disclosure relates to a method of converting glycerol into organic reaction products. The method may include mixing glycerol with a monohydric alcohol. The mixture of glycerol and monohydric alcohol is then reacted in the presence of a heterogeneous nano-structured catalyst, wherein the monohydric alcohol is present at subcritical/supercritical temperatures and pressures. This converts the glycerol into one or more reaction products, wherein the reaction products include an oxygenated organic reaction product. Ninety percent or greater of the glycerol is converted.

24 Claims, 4 Drawing Sheets

(56) References Cited

U.S. PATENT DOCUMENTS

| | | | |
|---|---|---|---|
| 8,252,961 B2* | 8/2012 | Suppes | 568/861 |
| 8,445,400 B2* | 5/2013 | Devi et al. | 502/168 |
| 8,507,702 B2* | 8/2013 | Feng et al. | 554/167 |
| 2007/0238905 A1 | 10/2007 | Arredondo et al. | |
| 2010/0121087 A1 | 5/2010 | Banavali et al. | |
| 2010/0125145 A1 | 5/2010 | Yu et al. | |
| 2010/0270239 A1 | 10/2010 | Zhu et al. | |
| 2011/0065943 A1 | 3/2011 | Banavali et al. | |
| 2011/0098510 A1* | 4/2011 | Versteeg et al. | 568/679 |
| 2012/0193580 A1 | 8/2012 | Feng et al. | |
| 2012/0253057 A1 | 10/2012 | Feng et al. | |

OTHER PUBLICATIONS

Otera, "Transesterification," Chem. Rev. 93 (1993), pp. 1449-1970.
Davies, et al., "Continuous transesterification of ethyl alcohol and butyl acetate in a sieve plate column: II. Batch reaction kinetic studies," Trans. Inst. Chem. Eng. 51 (1973), pp. 271-274.
Freedman, et al., "Tranesterification kinetics of soybean oil," J. Am. Oil Chem. Soc. 63(1986), pp. 1375-1380.
Schmidt, et al., "Kinetics of ethanol and butyl acetate-a model system for reactive rectification," Chem. Ing. Tech.71 (1999), pp. 704-708.
Felizardo, et al., "Production of biodiesel from waste frying oils," Waste Management, vol. 26, Issue 5, 2006, pp. 487-494.
Phan, et al., "Biodiesel production from waste cooking oils," Fuel, vol. 87, Issues 17-18, 2008, pp. 3490-3496.
Gryglewicz, "Alkaline-earth metal compounds as alcoholysis catalysts for eater oils synthesis," Appl. Catal. A 192 (2000), pp. 23-28.
Darnoko et al., Kinetics of palm oil transesterification in a batch reactor, J. Am. Oil Chem. Soc. 77 (2000), pp. 1263-1267.
Guan, et al., "Tri-potassium phosphate as a solid catalyst for biodiesel production from waste cooking oil," Fuel Processing Technology, vol. 90, Issue 4 (2009), pp. 520-524.
Georgogianni, et al. "Transesterification of soybean frying oil to biodiesel using heterogeneous catalysts," Fuel Processing Technology, vol. 90 Issue 5 (2009), pp. 671-676.
Dossin, et al., "Kinetics of heterogeneously MgO-catalyzed transesterification," Appl. Catal. B Environ. 62 (2006), pp. 35-45.
Reddy, et al., "Room-Temperature Conversion of Soybean Oil and Poultry Fat to Biodiesel Catalyzed by Nanocrystalline Calcium Oxide," Energy & Fuels 20 (2006), pp. 1310-1314.
Demirbas, "Biodiesel fuels from vegetable oils via catalytic and non-catalytic supercritical alcohol transesterifications and other methods: a survey," 44 (2003), pp. 2093-2109.
Kusdiana, et al., "Effects of water on biodiesel fuel production by supercritical treatment," Bioresour. Technol. 91 (2004), pp. 289-295.
Han, et al., "Preparation of biodiesel from soybean oil using supercritical methanol and carbon dioxide as cosolvent," Process Biochem 40 (2005), pp. 3148-3151.
Bunyakiat, et al., "Continuous production of biodiesel via transesterfication from vegetable oils in supercritical methanol," Energy & Fuels 20 (2006), pp. 812-817.
Warabi, et al., "Reactivity of triglycerides and fatty acids of rapeseed oil in supercritical alcohols," Bioresource Technol. 91 (2004), pp. 283-287.
Komers, et al., "Biodiesel from rapeseed oil and KOH 2. Composition of solution of KOH in methanol as reaction partner of oil," Eur. J. Lipid Sci. Technol. 103 (2001), pp. 359-462.
Kusdiana, et al., "Kinetics of transesterification in rapeseed oil to biodiesel fuels as treated in supercritical methanol," Fuel 80 (2001), pp. 693-698.
Kusdiana, et al., "Methyl esterification of free fatty acids of rapeseed oil as treated in supercritical methanol," Chem. Eng. Jpn., vol. 34, No. 3 (2001), pp. 383-387.

Coa, et al., "Preparation of biodiesel from soybean oil using supercritical methanol and co-solvent," Fuel 84 (2005), pp. 347-351.
Rathore, et al., "Syntheis of biodiesel from edible and non-edible oils in supercritical alcohols and enzymatic synthesis in supercritical carbon dioxide," Fuel 86 (2007), pp. 2650-2659.
Patil, et al., "Conversion of waste cooking oil to biodiesel using ferric sulfate and supercritical methanol processes," Fuel 89 (2019), pp. 360-364.
Demirbas, "Biodiesel from sunflower oil in supercritical methanol with calcium oxide," Energy Conv. Manag. 48 (2007), pp. 937-941.
He, et al., "Continuous production of biodiesel fuel from vegetable oil using supercritical methanol process," Fuel 86 (2007), pp. 442-447.
Suppes, et al., "Transesterification of soybean oil with zeolite and metal catalysts," Appl. Catal., 257 (2004), pp. 213-223.
Helwani, et al., "Technologies for production of biodiesel focusing on green catalytic techniques: A review," Fuel Processing Technology 90 (2009), pp. 1502-1514.
Ding, et al., "Modification of the Ultrastable Y Zeolite with Citric Acid in the Unbuffered System," J. Mol. Catal. vol. 11, No. 3 (1997) 163-164.
Xin-Mei, et al., "Optimization of nanopores and acidity of USY zeolite by citric modification," Catalysis Today 68 (2001) 145-154.
Noureddini, et al al, "Production Of Ethers Of Glycerol From Crude Glycerol—The By-Product Of Biodiesel Production"; University of Nebraska-Lincoln, Digital Commons@University of Nebraska-Lincoln, Papers in Biomaterials, Chemical and Biomolecular Engineering Research and Publications, Jan. 1, 1998, Paper 18, http://digitalcommons.unl.edu/chemeng_biomaterial/18.
Marulanda, et al; "Biodiesel Fuels Through A Continuous Flow Process Of Chicken Fat Supercritical Transesterification"; Energy Fuels 2010, 24, 253-260; energy&fuels article; 2009 American Chemical Society.
Chaudhari, et al Production Of Hydrogen and/or Syngas (H2 + CO) via Steam Gasification of Biomass-Derived Chars; Energy & Fuels 2003, 17, 1062-1067; 2003 American Chemical Society.
Hoang, et al, "Conversion of Glycerol To Alkyl-aromatics Over Zeolites"; 2010 American Chemical Society, Energy Fuels 2010, 24, 3804-3809.
Pathak, et al "Catalytic Conversion Of Glycerol To Value Added Liquid Products"; Applied Catalysis A; General 372 (2010) 224-238.
Barrault, et al Selective Oligomerization Of Glycerol Over Mesoporous Catalysts; Topics in Catalysis, vol. 27, Nos. 1-4, Feb. 2004, 137-142, 2004 Plenum Publishing Corporation.
Silva, et al "Glycerol Acetals As Anti-Freezing Additives For Biodiesel"; Bioresource Technoloty 101 (2010) 6225-6229, Science Direct.
Garcia, et al "New Class of Acetal Derived From Glycerin As A Biodiesel Fuel Component" 2008 American Chemical Society, Energy & Fuels 2008, 22, 4274-4280.
Mallon, et al "Driving Forces For Adsorption of Polyols Onto Zeolites From Aqueous Solutions", J. Phys. Chem. B 2010, 114, 1939-1945.
Li, et al "Effects Of Zeolite Membrane Structure On The Separation of 1,3-Propanediol From Glycerol And Glucose By Pervaporation"; Chem. Mater. 2001, 13, 1865-1873.
Gil, et al Acidic Hydroxyl Groups In Zeolites X and Y: A Correlation Between Infrared And Solid-State NMR Spectra; J. Phys. Chem. 1994, 98, 930-933.
http://en.wikipedia.org/wiki/2-Methyltetrahydrofuran—accessed on Jun. 1, 2011—Wikipedia, the free encyclopedia; (downloaded attachment from the web Jan. 10, 2013).

* cited by examiner

FUELS AND FUEL ADDITIVES PRODUCTION FROM GLYCEROL CONVERSION USING A MONOHYDRIC ALCOHOL AND HETEROGENEOUS CATALYSIS

FIELD OF INVENTION

The present disclosure relates to a process for the production of oxygenated fuels, components and oil additives from glycerol. In particular, the present disclosure relates to a process for the conversion of glycerol via sub/supercritical alcohol in the presence of a heterogeneous nano-structured catalyst.

BACKGROUND

Glycerol (glycerin) is a by-product of hydrocarbon ester production (biodiesel) via transesterification reaction from renewable vegetable oils and animal fats. Glycerol without further refinement is difficult to utilize as a fuel due to the potential release of acrolein when burned. In addition, if glycerol is left to settle, it may harden and cake, which may block fuel supply systems. Furthermore, impurities in the glycerol, as by-products of glycerol production, may lead to engine damage.

The increase in the production of biodiesel leads to a continued increase in the glycerol supply to the market, which may be well beyond the need for chemical byproducts. Using glycerol by-products to produce value added products, such as fuels or liquid chemicals may improve the economics of biodiesel production.

Value-added products of glycerol have been produced by pyrolysis, steam gasification and catalytic treatment. For example, hydrogen and syngas were produced from pyrolysis of glycerol with and without a carrier gas (nitrogen) in a fixed bed reactor at 400° C. to 500° C. In addition, the use of glycerol to form fuel or oil additives has been explored.

Glycerol conversions catalyzed by zeolite catalysts have also been explored. For example, the effect of the catalyst pore structure on product distribution during glycerol conversion was examined using HZSM-5, HY, HNaMOR and HZSM-22 catalysts at temperatures of 300 to 400° C. at atmospheric pressure or 2 MPa. Using the three-dimensional zeolites, HZSM-5 and HY, only oxygenates were produced at 300° C., irrespective of pressure. The oxygenates consisted of acetaldehyde, formaldehyde, propenal, acetol and relatively small amounts of heavier oxygenates. Upon increasing the temperature to 400° C., a hydrocarbon phase was formed and aromatics were identified, irrespective of the pressure.

In addition, one-dimensional medium-pore HZSM-22 catalysts have been found to be suitable for acrolein production, with 86% yield at 100% glycerol conversion. Three-dimensional medium-pore HZSM-5 results in a relatively high alkyl aromatic yield. Silica alumina produced the maximum acetaldehyde (24.5 g/100 g feed), γ-alumina produced the maximum acrolein (25 g/100 g feed) as shown in equation (1) below. Silica-alumina produced a formaldehyde yield of 9 g/100 feed and HY catalyst produced a relatively higher acetol yield of 14.7 g/100 g feed.

EQ. (1)

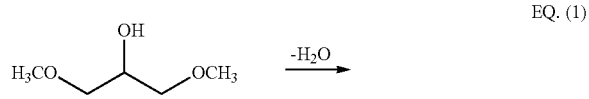
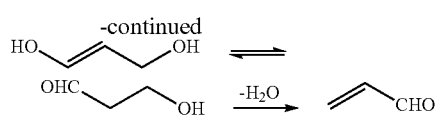

In the presence of aldehydes, further reaction with glycerol produces glycerol acetals, as shown in Equations (2) and (3), which may be useful as fuel additives.

EQ.(2)

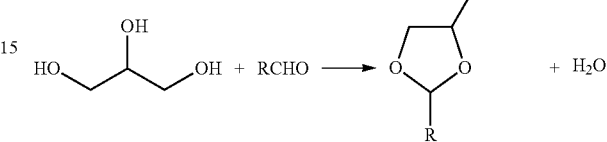

EQ.(3)

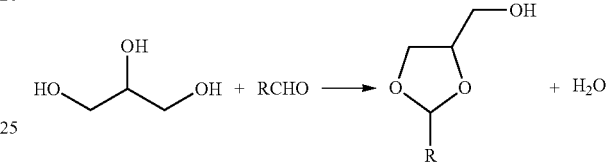

Furthermore, glycerol dehydration to methyl ethers under supercritical methanol conditions without the use of catalysts has been considered. The reaction of glycerol under these conditions resulted in the formation of methyl glycerol ethers, alcohols, and diglycerol related compounds.

However, a process for producing oxygenated fuels, fuel components and additives from glycerol with relatively improved product selectivity, and which can be made continuous, remains desirable.

SUMMARY

An aspect of the present disclosure relates to a method of converting glycerol into organic reaction products. The method includes mixing glycerol containing hydroxyl groups with methanol and reacting the glycerol and methanol in the presence of a heterogeneous nano-structured catalyst, wherein the methanol is present at a temperature of 200° C. or greater and a pressure of 1,140 psia or greater. One or more of the hydroxyl groups of the glycerol is converted into alkyl, alkyl ether, carbonyl, cyclic ether or alkene functionality. The conversion of glycerol may be made continuous and is achieved at a level of 90% or greater.

Another aspect of the present disclosure also relates to a method of converting glycerol into organic reaction products. The method includes mixing glycerol containing hydroxyl groups with a monohydric alcohol and reacting the glycerol and monohydric alcohol in the presence of a heterogeneous nano-structured catalyst. The monohydric alcohol is present as a supercritical fluid. These conditions provide for conversion of the glycerol into one or more reaction products, wherein one or more of the glycerol hydroxyl groups are converted into alkyl, alkyl ether, carbonyl, cyclic ether or alkene functionality. The conversion of glycerol may be made continuous and is achieved at a level of 90% or greater.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

The present disclosure relates to a process for the conversion of glycerol in the presence of a heterogeneous nanostructured catalyst, wherein monohydric alcohol is present as a supercritical fluid. In addition, in some embodiments where the monohydric alcohol is methanol, the methanol is present at subcritical or supercritical temperatures of 200° C. or greater and at pressures of 1,140 psia or greater. The process may be made continuous. Under such conditions, one or more of the hydroxyl groups of glycerol may undergo reactions to provide alkyl (e.g. —CH$_3$), alkyl ether (e.g. —OCH$_3$), carbonyl (—CO—), cyclic ether and/or alkene (e.g. CH$_2$=CH—) functionality with conversion levels of 90-100%.

The process produces organic reaction products which may be used as oxygenated fuels, fuel additives and oil additives. Fuels as understood herein are compositions that undergo combustion, i.e., exothermic chemical reactions between the fuel and an oxidant. Combustion takes place, for example, in engines or furnaces. Oxygenated fuels are understood as fuels that contain oxygen in their chemical structure. Fuel additives are compounds used in fuel compositions which may alter a fuel property. Oil is understood herein as compositions that are relatively viscous, having a viscosity greater than water at 25.0° C., and suitable for lubricants, including lubricants for components that are used in or near combustion environments. Oil additives may therefore alter a property of a selected oil.

Glycerol is understood as a polyol including three hydroxyl groups, generally represented by the following formula EQ. 4.

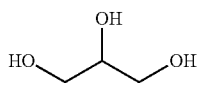

EQ.(4)

As noted above, glycerol is obtained as a byproduct of the production of hydrocarbon esters via transesterificaton reaction from vegetable oils and animal fats. For example, as illustrated in the general reaction scheme depicted in FIG. 1, triglycerides (T) are treated with an alcohol (—OH), such as a monohydric alcohol including methanol, ethanol, n-propyl alcohol, n-butyl alcohol, n-pentyl alcohol with a catalytic base (B) to produce ethyl esters of fatty acids (E) and glycerol (G). It is noted that R1-CO—O—, R2-CO—O— and R3-CO—O— may contain 4-28 carbon atoms in the illustrated triglyceride structure. The monohydric alcohol, R'OH is such that R' may be —CH$_3$, —CH$_2$CH$_3$, —CH$_2$CH$_2$CH$_3$, —(CH$_2$)$_3$—CH$_3$ and/or —(CH$_2$)$_4$—CH$_3$.

Figure 1:
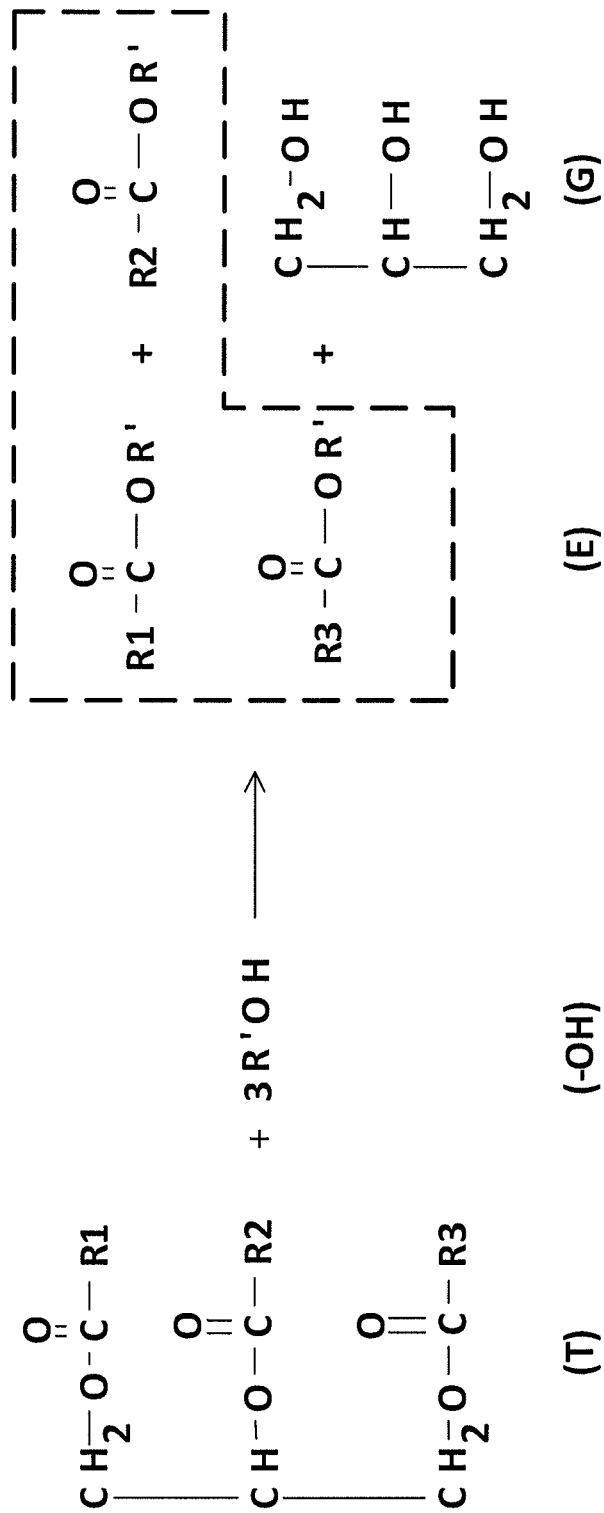
FIG. 1 is a schematic of a reaction scheme for producing glycerol from triglycerides.

It is noted that the reaction scheme in FIG. 1 may be made continuous and reference is made to U.S. application Ser. No. 13/074,205 directed at the continuous production of bio-derived esters via supercritical solvent processing using solid heterogeneous catalysis, whose teachings are incorporated by reference. As noted therein, a continuous transesterification reaction is employed for trans-esterifying a triglyceride comprising continuously providing a triglyceride and continuously providing a monohydric alcohol, such as methanol. This may then be followed by continuously mixing the triglyceride and monohydric alcohol in the presence of nanostructured transesterification catalyst where the catalyst is present with a largest cross-sectional dimension of 50 nm to 200 nm and wherein the monohydric alcohol (e.g. methanol) is present as a supercritical fluid (temperature of at least 240° C. and pressure of at least 1140 psia). The nanostructured catalyst may include zeolite, hydrotalcite and titanosilicate. This is then followed by trans-esterifying the triglyceride with the monohydric alcohol and generating mono-ester derivatives of the triglyceride. The continuously produced glycerol in this reaction scheme may now serve as the basis for the continuous conversion of such glycerol herein. In addition, the glycerol utilized herein may be obtained from any transesterification process. It may also be obtained from other processes such as saponification of fats.

Figure 2:
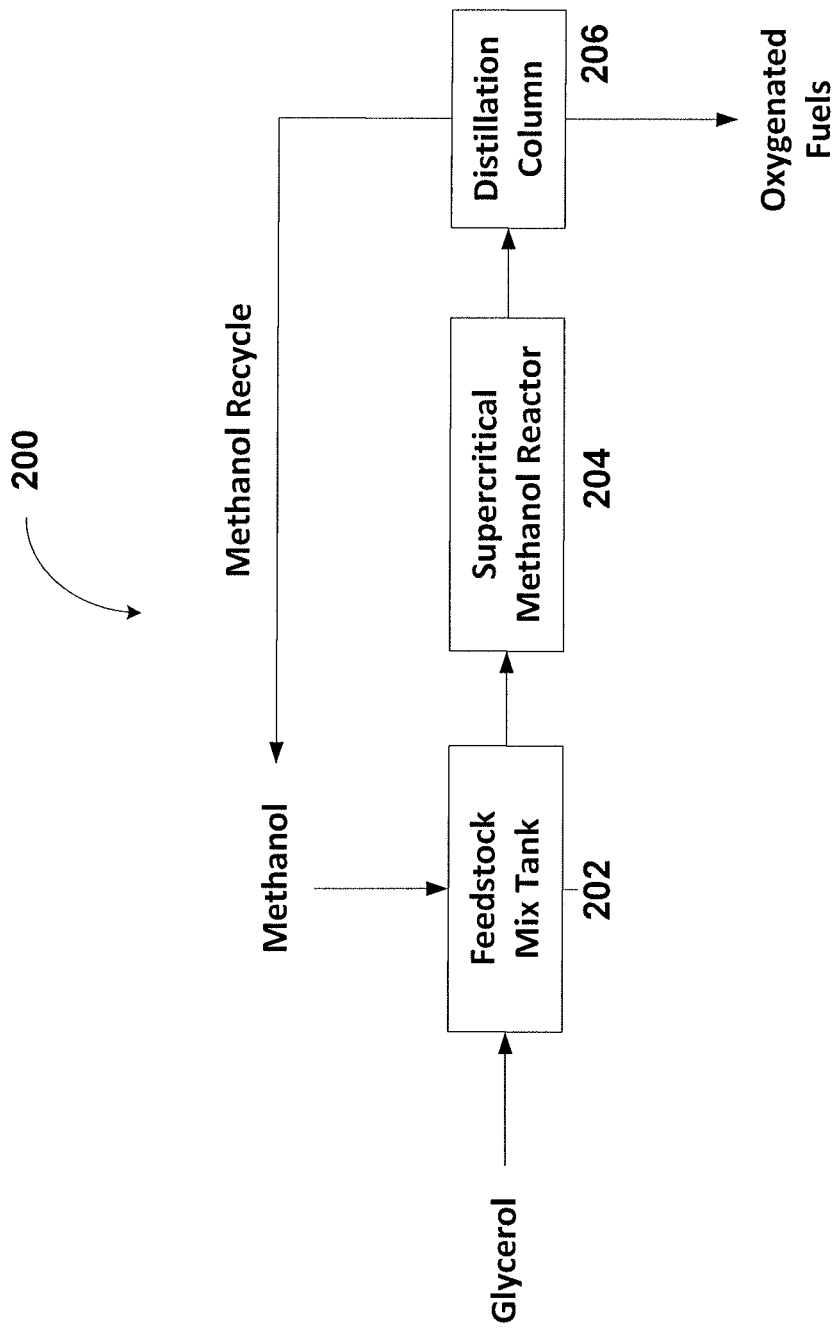
FIG. 2 is a schematic of a general process of converting glycerol into oxygenated organic reaction products.

FIG. 2 illustrates a general process 200 for converting glycerol into oxygenated fuels. Glycerol and monohydric alcohol may be added to a feedstock tank 202. Preferably, the monohydric alcohol comprises at least one alcohol selected from the group consisting of methanol, ethanol, n-propyl alcohol, n-butyl alcohol and n-pentyl alcohol. More preferably, the alcohol is methanol.

The feedstock may be combined and fed into a reactor 204. The monohydric alcohol is present as a supercritical fluid during the conversion of the glycerol in the reactor. The presence of the monohydric alcohol as a supercritical fluid is reference to the use of the alcohol during the conversion of glycerol wherein the monohydric alcohol is present at or above its critical temperature and critical pressure. Table 1 outlines the various supercritical temperatures Tc and pressures Pc for the examples of monohydric alcohols disclosed herein.

TABLE 1

| Supercritical Conditions for Monohydric Alcohols | | |
|---|---|---|
| Monohydric Alcohol | Tc (° C.) | Pc (psia) |
| Methanol | 240 | 1,140 |
| Ethanol | 241 | 914 |
| n-propyl alcohol | 264 | 754 |
| n-butyl alcohol | 289 | 653 |
| n-pentyl alcohol | 307 | 566 |

Where the monohydric alcohol is methanol, conversion of the glycerol in the reactor may occur at subcritical conditions or supercritical conditions. Specifically, glycerol conversion may occur at temperatures of at or above 200° C., such as in the range of 200° C. to 400° C., including all values and increments therein, and preferably, at temperatures above 240° C., such as at temperatures above 250° C. to 375° C., 300° C. to 350° C., etc. The reaction temperature should be preferably maintained at or below 400° C. to avoid methanol consumption via the methanol-to-gasoline (MTG) process when methanol is used. In addition, conversion of the glycerol using methanol may preferably occur at pressures at or greater than 1,140 psia, such as in the range of 1,140 psia to 3,500 psia, including all values and increments therein, and preferably, at pressures of 2,000 psia to 3,500 psia, pressures of 2,500 psia to 3,250 psia, etc.

Figure 3:
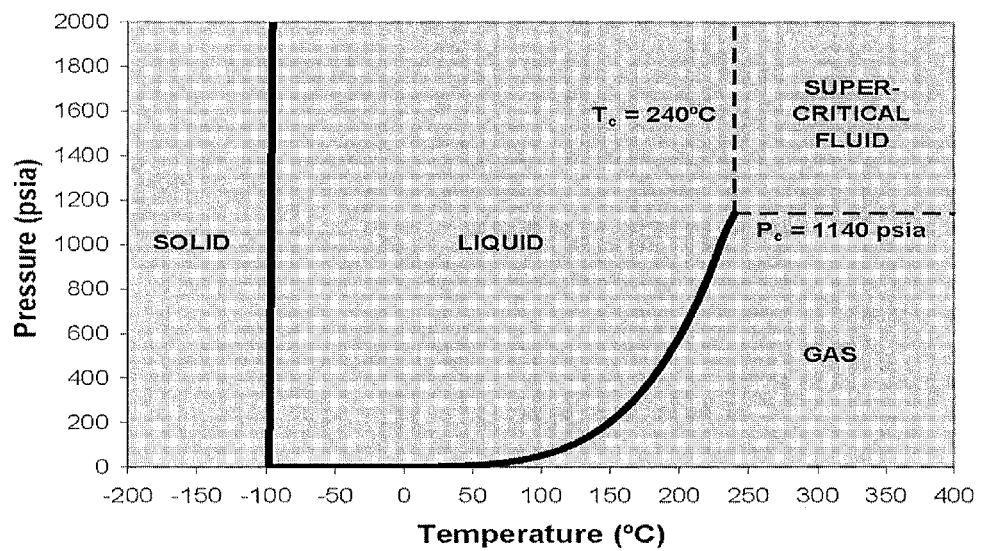
FIG. 3 is a phase diagram of methanol illustrating supercritical fluid conditions.

At such temperatures and pressures, methanol is at sub-critical or supercritical state. FIG. 3 illustrates a phase diagram for methanol. As seen in the diagram, methanol is at supercritical state or is a supercritical fluid at critical temperatures of 240° C. or greater and critical pressures of 1,140 psia or greater. In the supercritical state, distinct gas and liquid phases do not exist and the methanol will exhibit gas-like diffusivity and liquid-like viscosity.

Referring again to FIG. 2, a solid heterogeneous nano-structured catalyst is packed in the reactor 204. The catalyst to glycerol ratio, in embodiments, may range from 1:5 to 1:150, including all values and ranges therein. A heterogeneous nano-structured catalyst may be understood as a catalyst that does not dissolve in the monohydric alcohol and whose dimensions (e.g. cross-sectional diameter) may be expressed in nanometers as noted herein. The heterogeneous nano-structured catalyst may be selected from 1)zeolites, 2)titano-silicate and 3)hydrotalcite. Further, combinations of zeolites with alumina, silica and alumina-silica may also be utilized as a heterogeneous nano-structured catalyst herein. The heterogeneous nano-structured catalyst preferably exhibits a largest cross-sectional dimension in size of 50 nm to 200 nm, including all values and ranges therein at 1 nm size increments. Accordingly, the heterogeneous nano-structured catalyst herein may be present with a largest cross-sectional diameter of 50 nm, 51 nm, 52 nm, and so on up to 200 nm. More preferably, the heterogeneous nano-structured catalysts herein are those which may have a largest cross-sectional size of 50 nm to 100 nm. In addition, the catalyst may be formed into a given shape in the presence of a binder, such as silica gel. The shapes may include rods, cylinders, etc. depending on the reactor.

Zeolites may generally be understood as aluminosilicate based mineral. Typically, zeolites have a unit consisting of a tetrahedral complex of Si4+ and Al3+ in coordination with four oxygen atoms. The tetrahedral units of $(SiO_4)$ and $(AlO_4)^-$ may be linked to each other by shared oxygen atoms to form three-dimensional networks. The networks produce channels and cavities of molecular dimensions. Charged compensating cations are found inside the channels and cavities of the zeolitic materials. The various possible linkages between the primary tetrahedral structure determine the different zeolite structures, which can have different surface areas, pore size, and/or pore shape. Besides silicon and aluminum, other atoms can be incorporated into lattice positions.

In general, suitable zeolites will be of the faujasite structure with a $SiO_2/Al_2O_3$ mole ratio in the range of about 2 to 8. With regard to structural classification, those zeolites with a double 6-ring or faujasite structure are generally suitable for use herein. Such zeolites characteristically have pore diameters in excess of 6 angstroms, which is appropriate for admission of a monohydric alcohol. Type X has a typical oxide formula $Na_2O.Al_2O_3.2.5SiO_2.6H_2O$ with $SiO_2/Al_2O_3$ in the range of 2.0-3.0. Type Y has a typical oxide formula $Na_2O.Al_2O_3.4.8SiO_2.8.9H_2O$ with $SiO_2/Al_2O_3$ ranging from 3.0-6.0.

A particularly preferred zeolite includes faujasite NaX which is a hydrated sodium and calcium aluminosilicate mineral. As noted above, the empirical formula for faujasite NaX is $Na_2O.Al_2O_3.2.4SiO_2.2.5H_2O$. The faujasite NaX may also preferably include potassium and/or cesium to increase its catalytic activity. The faujasite NaX may also undergo hydrothermal treatment, extraction by acid complexation or treatment with citric acid in an unbuffered media. Such is observed to optimize the acidity and nanopore distribution. An optimization of the acidity may result in an adjustment in the reaction, reducing coking. An optimization of the nanopore distribution results in a relatively more uniform distribution of the pores and channels in the catalyst. This may be achieved by treatment with citric acid under hydrothermal conditions for 2 to 3 days.

Anionic clays may also be employed as the heterogeneous nano-structured catalyst, one of which is a hydrotalcite. A hydrotalcite may be understood as a layered double hydroxide with positively charged layers and charge balancing anions in the interlayer region. They may have the general formula $[M^{2+}_{1-x}M^{3+}_x(OH)_2]^{q+}(X^{n-})_{q/n}.yH_2O$. Typically, $M^{2+}$ is $Ca^{2+}$, $Mg^{2+}$, $Mn^{2+}$, $Fe^{2+}$, $Co^{2+}$, $Ni^{2+}$, $Cu^{2+}$ or $Zn^{2+}$ and q=x and y=2-4.

One preferred hydrotalcite is a magnesium-aluminum hydrotalcite having the general formula (EQ. 5):

$$[Mg_{(1-x)}Al_x(OH)_2]^{x+}(CO_3)_{x/n}^{2-} \qquad EQ(5).$$

where x may be 0.5 or less, such as in the range of 0.1 to 0.50 including all values and increments therein, and n has a value of 2.0.

One may also employ, as the heterogeneous nano-structured catalyst, a porous titanosilicate which may be generally understood as a titanosilicate (ETS-10) with a three-dimensional 12 ring channel system containing micropores. ETS-10 is understood to exhibit a chemical formula of $(Na_{1.5}K_{0.5})TiSi_5O_{13}.xH_2O$ having a mixture of two polymorphs with tetragonal and monoclinic symmetry. The ETS-10 herein may also be enhanced in its catalytic activity through the use of potassium and cesium.

Furthermore, the catalyst may include a combination of a zeolite and an oxide. The zeolite includes one of zeolite X or zeolite Y. The oxide includes one of alumina, silica or alumina-silica. The empirical formula for alumina is $Al_2O_3$ and the empirical formula for silica is $SiO_2$. Alumina-silica may be understood as aluminosilicate. The ratio of zeolite to the oxide may be in the range of 1:1 to 10:1, including all values and ranges therein.

Without being limited to any particular theory, in some embodiments, the glycerol may be converted into various reaction products through dehydration reactions, wherein the reaction of the glycerol with the monohydric alcohol in the presence of the catalyst forms water as a byproduct. In addition to water, additional reaction products of glycerol and monohydric alcohol over the heterogeneous nano-structured catalyst include one or more oxygenated reaction products and excess monohydric alcohol. A reaction product is understood herein to be the compositions resulting from or remaining after the reaction of the glycerol, monohydric alcohol and catalyst. The oxygenated organic reaction product(s) are optionally separated from the resulting reaction products into various components via distillation through a distillation column 206. Excess monohydric alcohol separated from the resulting reaction products is optionally recycled and may be added back into the feedstock. The above process may occur continuously or batch-wise.

Figure 4:
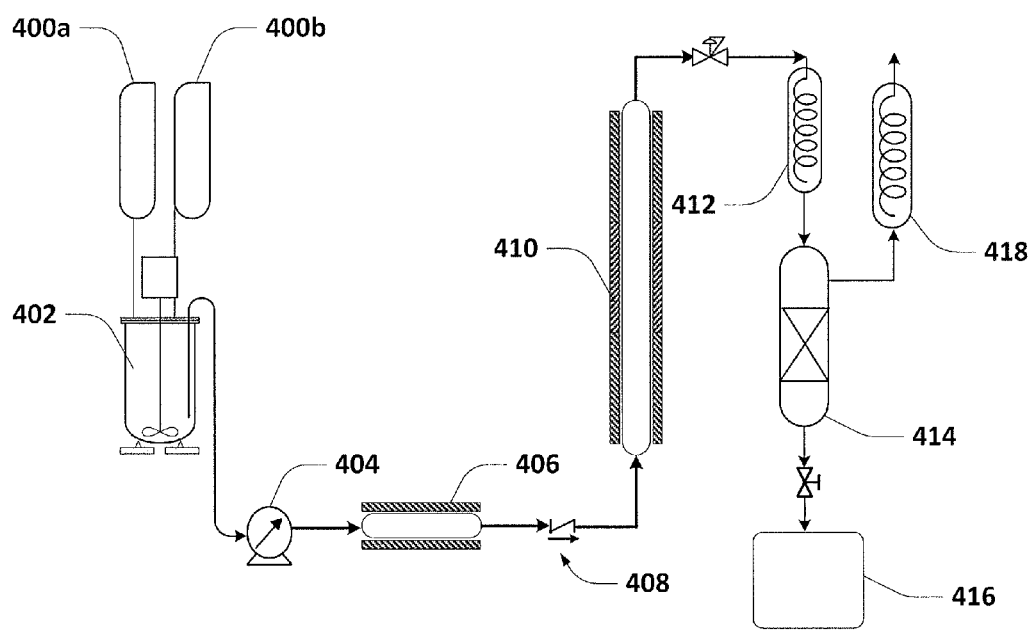
FIG. 4 is a schematic of an embodiment of a reaction system for converting glycerol into oxygenated reaction products.

A system 400 and method for continuous processing is described further herein with reference to FIG. 4.

As illustrated in FIG. 4, glycerol and monohydric alcohol are continuously fed from supply sources 400a, 400b, into a feed tank 402, such as a mixing tank, where the glycerol and monohydric alcohol are combined and stirred, improving mixing. The mixed glycerol and monohydric alcohol may then be pumped from the feed tank and into a pre-heater 406 via a pump 404. The pre-heater may be a single wall design and may be heated with an external furnace or jacketed for heating and cooling with a circulating heat transfer medium. The pre-heater may also include a resistance heater wrapped around the wall of the pipe or conduit through which the glycerol/monohydric alcohol mixture is transferred.

The glycerol/monohydric alcohol mixture is continuously pumped through a one-way valve 408, preventing the back flow of the mixture into the pre-heater 406 and the pump 404, and into a continuous flow reactor 410. A continuous flow reactor is understood as a reactor that may be used in a continuous flow mode with reagents flowing in and products being removed. A single phase flow in the tubular reactor may be configured to run upward or downward. Two-phase flow may be configured wherein one may have co-current up-flow, counter-current (liquid down, gas up) or co-current down flow.

The reactor may be a single wall design and may be heated with an external furnace or jacketed for heating and cooling with a circulating heat transfer medium. In addition, the reactor may be packed and, therefore contain a fixed bed of the above described heterogeneous nano-structured catalyst. Flow rates through the reactor may be in the range of 0.5 mL/min. to 5.0 mL/min. including all values and ranges therein. Residence time of the glycerol in the reactor may be in the range of 10 to 30 minutes, including all values and ranges therein. Preferably, the reactor 410 may include a ⅜ inch diameter stainless steel fixed-bed reactor.

The reactor may include one or more thermocouples inserted through the side wall of the reactor to monitor. For example, thermocouples may be inserted through thermowells welded to the reactor tube. Pressure within the reactor may be controlled with a pressure controller or pump and detected with a pressure transducer. A pressure gage may also be installed in-line to ensure that appropriate pressures are maintained.

The reaction products may pass through a heat exchanger 412 to reduce the temperature of the reaction products to the range of 40° to 60° C., including all values and increments therein. The reaction products are optionally separated in the distillation column 414, if not already separated in a distillation reactor. The oxygenated organic reaction products are directed from the distillation column into one or more product receivers 416. Monohydric alcohol is directed to a condenser 418 where the monohydric alcohol may be condensed from a gas to a liquid state and then, optionally recycled and fed back into the feed tank 402 for further use.

In embodiments, the oxygenated organic reaction products may selectively include up to 15 reaction products or in the range of 2 to 15 reaction products, including all values and increments therein, such as 5, 6, 7, 8 etc. Some of the oxygenated reaction products include a composition having the following general equation (EQ. 6):

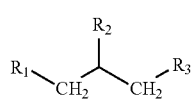

EQ.(6)

wherein $R_1$ is selected from the group consisting of OH and $OCH_3$, $R_2$ is selected from the group consisting of H, OH, $OCH_3$, and $CH_3$, and $R_3$ is selected from the group consisting of H and $OCH_3$. Other oxygenated reaction products include a composition having the following general equation (EQ. 7):

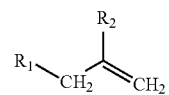

EQ.(7)

wherein $R_1$ is selected from the group consisting of OH and $OCH_3$, $R_2$ is selected from the group consisting of H, OH, $OCH_3$, and $CH_3$, and $R_3$ is selected from the group consisting of H and $OCH_3$.

In certain preferred embodiments, the reaction product includes one or more of the following: 2-propanol-1,3-dimethoxy, 1,2-propane-diol, propane-1,2,3-trimethoxy, 1,2-propanediol-3-methoxy, 1-propanol-2-methyl, 2-propen-1-ol-2-methyl, 2-propen-1-ol and 1-propanol. Furthermore, the reaction products may include propanoic acid-2-methyl-methyl ester and 2-methoxytetrahydrofuran.

In the context of the use of sub/supercritical monohydric alcohol herein, the conversion rates of the glycerol in the presence of a heterogeneous nano-structured catalyst is observed to significantly increase in the sub/supercritical monohydric alcohol medium. Conversion rates of 90% or greater of the glycerol are achieved, such as in the range of 90 to 100%, including all values and increments therein, such as 92%, 98%, 99%, etc.

The process herein results in relatively more selective production of oxygenated fuels, fuel components and oil additives in the presence of the heterogeneous nano-structured catalyst. In using the sub/supercritical monohydric alcohol process, relatively good contact is provided between the miscible reactants, mass transfer is relatively more efficient, and relatively improved heat exchange occurs. This results in the glycerol being converted into relatively more beneficial products, reduces hot spots in the heterogeneous nano-structured catalyst increasing catalyst life and reduces coking, causes fewer side reactions to occur improving the selectivity of the formed products, and relatively overall energy use is lower.

One or more of the oxygenated reaction products herein may be added to a fuel as part of the base fuel composition itself or added to a fuel composition as an additive. For example, the oxygenated organic reaction products may form 1 to 100% by weight of the total fuel composition, including all values and ranges therein, and preferably in the range of 0.5 to 20% by weight, 10 to 20% by weight, etc. Furthermore, one or more of the oxygenated organic reaction products may also be used as additives to a base oil stock. The oxygenated organic reaction products may form 1 to 90% by weight of the total oil composition, including all values and ranges therein, and preferably in the range of 0.5 to 20% by weight, 10 to 20% by weight, etc.

EXAMPLES

Example 1

Glycerol and methanol were fed to a ⅜ inch diameter stainless steel fixed-bed reactor continuously at supercritical methanol conditions (300° C., 3000 psia) without catalyst. The following compounds, set forth in Table 2, were found by GC-MS analysis of the product stream.

TABLE 2

Compounds produced by etherification of glycerol
with methanol under supercritical conditions.

| Compound | Retention Time (min) | Concentration (μg/mL) | Structure |
|---|---|---|---|
| 1,2-propanediol-3-methoxy | 12.402 | 1872 | H₃CO-CH₂-CH(OH)-CH₂-OCH₃ |
| Dimetnyl ether | 2.610 | 1132 | H₃C-O-CH₃ |

It was found that the extent of glycerol conversion was minimal under the indicated circumstances where no catalyst was employed.

Example 2

Glycerol was fed to a supercritical methanol reactor packed with zeolite X catalyst at 300° C., 3000 psia. The following compounds, set forth in Table 3, were detected by GC-MS analysis in the product stream.

TABLE 3

Compounds produced by the etherification of glycerol with methanol under supercritical conditions in the present of a catalyst.

| Compound | Retention Time (min) | Structure |
|---|---|---|
| 2-butanol (E) | 3.742 | CH₃-CH(OH)-CH₂-CH₃ |
| 2-propen-1-ol | 4.522 | CH₂=CH-CH₂-OH |
| 2-propen-1-ol-2-methyl | 5.629 | CH₂=C(CH₃)-CH₂-OH |
| 2-propanol-1,3-dimethoxy | 8.741 | H₃CO-CH₂-CH(OH)-CH₂-OCH₃ |
| 2-methoxytetrahydrofuran | 4.728 | tetrahydrofuran-O-CH₃ |
| propanoic acid-2-methyl-methyl ester | 4.017 | H₃CO-C(=O)-CH(CH₃) |

It was found that glycerol was converted to nearly 100% with no detectable glycerol in the product.

Example 3

Glycerol was fed to a supercritical methanol reactor packed with ETS-10 catalyst at 300° C., 3000 psia. The following compounds, set forth in Table 4, were detected by GC-MS analysis in the product stream.

TABLE 4

Compounds produced by the etherification of glycerol with methanol under supercritical conditions in the present of a catalyst.

| Compound | Retention Time (min) | Concentration (μg/mL) | Structure |
|---|---|---|---|
| 1-propanol | 4.591 | 1708 | H₃C-CH₂-CH₂-OH |
| 2-propen-1-ol | 4.874 | 2043 | CH₂=CH-CH₂-OH |
| 2-propen-1-ol-2-methyl | 5.071 | 7971 | CH₂=C(CH₃)-CH₂-OH |
| 2-propanol-1,3-dimethoxy | 8.801 | 1884 | H₃CO-CH₂-CH(OH)-CH₂-OCH₃ |
| 1,2-propanediol | 9.993 | 1270 | H₃C-CH(OH)-CH₂-OH |
| 1,2-propanediol-3-methoxy | 12.531 | 11782 | HO-CH₂-CH(OH)-CH₂-O-CH₃ |

It was found that 92.9% of the glycerol was converted.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of converting glycerol, comprising:
   mixing glycerol containing hydroxyl groups with methanol;
   reacting said glycerol and methanol in the presence of a heterogeneous nano-structured catalyst, wherein said methanol is present at a temperature of 200° C. or greater and a pressure of 1,140 psia or greater;
   converting said glycerol into one or more reaction products, wherein one or more of said hydroxyl groups of said glycerol is converted into alkyl, alkyl ether, carbonyl, cyclic ether or alkene functionality; and
   wherein 90% or greater of said glycerol is converted to said reaction products containing said converted hydroxyl functionality.

2. The method of claim 1, wherein said methanol is present at a temperature in the range of 200° C. to 400° C. and a pressure in the range of 2,000 psia to 3,500 psia.

3. The method of claim 1, wherein said methanol is present as a supercritical fluid.

4. The method of claim 1, wherein said heterogeneous nano-structured catalyst comprises a zeolite mineral.

5. The method of claim 4, wherein said heterogenous nano-structured catalyst includes a zeolite and an oxide, wherein said zeolite is selected from the group consisting of zeolite X and zeolite Y, and said oxide is selected from one or more of the following: alumina, silica and aluminosilicate.

6. The method of claim 1, wherein said heterogeneous nano-structured catalyst comprises zeolite-X of the formula $Na_2O \cdot Al_2O_3 \cdot 2.5SiO_2 \cdot 6H_2O$ where $SiO_2/Al_2O_3$ is in the range of 2.0-3.0.

7. The method of claim 1, wherein said heterogeneous nano-structured catalyst comprises faujasite-NaX of the formula $Na_2O.Al_2O_3.2.4SiO_2.2.5H_2O$.

8. The method of claim 1, wherein said heterogeneous nano-structured catalyst comprises a hydrotalcite of the general formula $[M^{2+}_{1-x}M^{3+}_x(OH)_2]^{q+}(X^{n-})_{q/n}.yH_2O$ wherein $M^{2+}$ is one of $Ca^{2+}$, $Mg^{2+}$, $Mn^{2+}$, $Fe^{2+}$, $Co^{2+}$, $Ni^{2+}$, $Cu^{2+}$ or $Zn^{2+}$ and q=x and y=2-4.

9. The method of claim 1, wherein said heterogeneous nano-structured catalyst comprises magnesium-aluminum hydrotalcite of the general formula $[Mg_{(1-x)}Al_x(OH)_2]^{x+}(CO_3)_{x/n}^{2-}$ where x has a value of 0.25-0.55 and n has a value of 2.0.

10. The method of claim 1, wherein said heterogeneous nano-structured catalyst comprises titanosilicate ETS-10.

11. The method of claim 1, wherein one of said reaction products is excess methanol and said excess methanol comprises a portion of said methanol with which said glycerol is mixed.

12. The method of claim 1, wherein said oxygenated reaction product includes methyl glycol ethers.

13. The method of claim 1, wherein said oxygenated reaction product includes a composition having the following general equation:

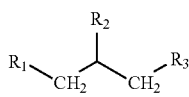

wherein $R_1$ is selected from the group consisting of OH and $OCH_3$, $R_2$ is selected from the group consisting of H, OH, $OCH_3$, and $CH_3$, and $R_3$ is selected from the group consisting of H and $OCH_3$.

14. The method of claim 1, wherein said reaction product includes a composition having the following general equation:

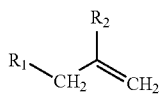

wherein $R_1$ is selected from the group consisting of OH and $OCH_3$, $R_2$ is selected from the group consisting of H, OH, $OCH_3$, and $CH_3$, and $R_3$ is selected from the group consisting of H and $OCH_3$.

15. The method of claim 1, wherein said oxygenated reaction product includes one or more of the following: 2-propanol-1,3-dimethoxy, 1,2-propane-diol, propane-1,2,3-trimethoxy, 1,2-propanediol-3-methoxy, 1-propanol-2-methyl, 2-propen-1-ol-2-methyl, 2-propen-1-ol and 1-propanol.

16. The method of claim 1, wherein said reaction product includes propanoic acid-2-methyl-methyl ester.

17. The method of claim 1, wherein said reaction product includes 2-methoxytetrahydrofuran.

18. The method of claim 1 comprising supplying a continuous source of glycerol and continuously mixing said glycerol with methanol in the presence of said heterogeneous nano-structured catalyst and continuously converting said glycerol into said reaction products.

19. The method of claim 1, further comprising adding one or more of said oxygenated reaction products to a fuel.

20. The method of claim 1, further comprising adding one or more of said oxygenated reaction products to an oil.

21. The method of claim 1 wherein said heterogenous nano-structured catalyst has a largest cross-sectional dimension of 50 nm to 200 nm.

22. A method of converting glycerol, comprising:
mixing glycerol containing hydroxyl groups with monohydric alcohol;
reacting said glycerol and monohydric alcohol in the presence of a heterogeneous nano-structured catalyst, wherein said monohydric alcohol is present as a supercritical fluid;
converting said glycerol into one or more reaction products, wherein one or more of said hydroxyl groups of said glycerol is converted into alkyl, alkyl ether, carbonyl, cyclic ether or alkene functionality; and
wherein 90% or greater of said glycerol is converted to said reaction products containing said converted hydroxyl functionality.

23. The method of claim 22, wherein said monohydric alcohol is selected from the group consisting of methanol, ethanol, n-propyl alcohol, n-butyl alcohol, and n-pentyl alcohol.

24. The method of claim 22 wherein said heterogeneous nano-structured catalyst has a largest cross-sectional dimension of 50 nm to 200 nm.

* * * * *